United States Patent [19]

Oertli

[11] Patent Number: 4,576,696

[45] Date of Patent: Mar. 18, 1986

[54] PROCESS FOR THE PREPARATION OF A BIOLOGICALLY ACTIVE EXTRACT

[75] Inventor: Robert Oertli, Möhlin, Switzerland

[73] Assignee: Solco Basel AG, Basel, Switzerland

[21] Appl. No.: 652,343

[22] Filed: Sep. 19, 1984

[30] Foreign Application Priority Data

Oct. 5, 1983 [CH] Switzerland .................. 5413/83

[51] Int. Cl.$^4$ .............................................. B01D 13/02
[52] U.S. Cl. ............................ 204/182.6; 204/182.4; 424/95; 424/101; 424/103; 424/105; 424/106; 424/107
[58] Field of Search ............. 204/180 P, 182.4, 182.6; 210/634, 645, 650, 748, 781, 787, 927, 173; 424/95, 101, 106, 105, 107, 103

[56] References Cited

U.S. PATENT DOCUMENTS 3,799,806  3/1974  Madsen ........................... 204/180 P
4,054,648  10/1977  Nagasawa et al. ................. 424/105

FOREIGN PATENT DOCUMENTS 559954  6/1977  U.S.S.R. .

Primary Examiner—John F. Niebling
Assistant Examiner—B. J. Boggs, Jr.
Attorney, Agent, or Firm—Ladas & Parry

[57] ABSTRACT

A mammal organ, for example the thymus, or a cell culture is comminuted to form a slurry, accompanied by cell disintegration, high molecular weight substances are precipitated by heating and removed by centrifuging, and residual substances of molecular weight greater than 10,000 are separated out by ultrafiltration; finally, the salts are substantially removed by electrodialysis. A biologically active, low-salt, sterile, pyrogen-free and antigen-free complete extract is obtained and, in contrast to all known processes, no foreign substance or auxiliary, other than water—not even a preservative or a carrier for separation methods—is used.

8 Claims, 8 Drawing Figures

PROCESS FOR THE PREPARATION OF A BIOLOGICALLY ACTIVE EXTRACT

Processes for the preparation of organ extracts have been known for a substantial time. Various authors have contented themselves with simple extraction, mostly of an aqueous solution; often, all that was carried out was mechanical treatment of the organ, this being so especially in purely scientific work. The increasing importance of transplants of bone marrow, kidneys, heart, blood and the like and the recognition of the biological activity of various organs, especially of the thymus (Hess, 1968), together with the rapid development of cellular immunology, have resulted in intensive research into methods and processes for the preparation of biologically active organ extracts for therapeutic use. Depending on the requirements the prepared product has to meet, biologically poorly tolerated agents such as acids, acetone or even alcohol may be employed in the method of preparation. The products differ from a complete extract essentially in that they are either a pure, precisely characterized compound or an analytically precisely defined mixture of substances from the corresponding organ.

In contrast, the subject of the present invention is a process for the preparation of a biologically active, low-salt, pyrogen-free and nitrogen-free complete extract of mammal organs or of cell cultures. The extract consists of a mixture of biologically active substances having a molecular weight of less than 10,000 Daltons and is in particular distinguished in that apart from water it contains absolutely no foreign substances or auxiliaries or any other added substances.

We have in fact found, surprisingly, that the precipitation reactions hitherto customary in the preparation of organ extracts can be entirely omitted and be advantageously replaced by thermal denaturation in a heat exchanger with successively working heat transfer medium and cooling medium.

Accordingly, the novel process comprises
(a) comminuting the starting material, procured under as low-germ conditions as possible or, in the case of cell cultures, sterile conditions, with disintegration of the cells,
(b) heating the comminuted and disintegrated material rapidly to a temperature in the range from 70° to 90° C., preferably to about 80° C., and after the desired time rapidly cooling it again to a low temperature, for example 4 or 10° C., whereby, on the one hand, thermolabile constituents, for example proteins, are precipitated, and on the other hand the bacteria and enzymes are inactivated without being able to proliferate again or become active again in the medium temperature range,
(c) separating the precipitated products from the solution by centrifuging,
(d) removing the substances which have remained in the solution and have a molecular weight of greater than 10,000 Daltons by ultrafiltration, whereby the antigens and endotoxins are eliminated and
(e) substantially removing the dissolved salt ions from the remaining solution by electrodialysis.

Even though the extract obtained is sterile and pyrogen-free as a result of the process of preparation in itself, the said process can, if desired, be followed by a sterile filtration as a safety measure.

In sharp contrast to the processes hitherto known, no foreign substance whatsoever—except for water—is introduced into the system according to the present invention. In particular, neither preservatives nor any chemical additives, for instance bactericides (for example azides) which usually ensure sterility and freedom from pyrogens, are added to the starting material or the various intermediates or the end product: the extract obtained is pyrogen-free and sterile because of the method of preparation. The absence of any addition of foreign substance in the course of the process gives the patient the advantage of greater safety, the registration authority the advantage of easier assessment and the manufacturer the advantage of lower expense.

A feature of the process according to the invention to be mentioned particularly is that the use of any carrier material, and the use of any column chromatography separation, is deliberately dispensed with. In this respect also the novel extraction process is in clear contrast to the known processes; this important difference is hence also reflected in the composition of the process product.

In fact, if the substances in the extract are classified in groups according to their basic physicochemical behavior, the following picture of the extract obtained according to the process emerges:

| | | |
|---|---|---|
| 1st group: | hydrophilic substances (largely ninhydrin-positive) | Part A in FIG. 1 |
| 2nd group: | salt ions; | |
| 3rd group: | hydrophobic substances (largely anisaldehyde-positive) | Part B in FIG. 1 |

Viewed diagrammatically, the distribution of the three groups is as shown in the attached FIG. 1.

If the salt ions, some of which are undesirable, are removed by column chromatography, for example over Sephadex ®, only the part marked A of the substances remains in the end product, while part B, namely, in addition to the salt ions, all hydrophobic substances and even a proportion of ninhydrin-positive substances, is lost. However, substances present in part B demonstrably possess a biological action; their loss therefore means a significant disadvantage for the corresponding product relative to the complete extract obtained by the present process.

In addition, column chromatography introduces a foreign substance, namely the carrier material, into the system. This as a rule means the danger of bacterial contamination of the product, leading to pyrogen-containing end products, while the end product obtained according to the present invention is pyrogen-free.

Finally, as a result of all chromatographic separation being dispensed with, the major expenditure of time associated with elution, and the work subsequently required to remove the large amounts of eluant (water) used, are dispensed with.

Accordingly, what is obtained for the first time is a complete extract which—when compared with the products from the known extraction processes—contains all biologically active substances, in particular all low molecular weight peptides (<10,000 Daltons) and also, because of its low salt content and its freedom from pyrogens and antigens, can be administered directly without additional measures.

If one reflects on the difficulties and work which the removal of pyrogenic material from biological products for parenteral administration generally causes (see, for example, German Offenlegungsschrift No. 3,229,132), and also on the numerous sensitizing or harmful effects of the conventionally added preservatives (see, inter alia, Hagers Handbuch per pharmazeutischen Praxis, Springer Verlag, Berlin Heidelberg New York 1977, page 313), the special nature of the novel process and its superiority over known extraction processes become really evident.

The process is described in detail below.

The process can be used to prepare all sorts of organic extracts. The most important starting materials are the following organs and tissues: spleen, thymus, liver, heart, placenta, bone marrow and blood. However, extracts of cell cultures, especially of animal cell cultures, can also be prepared, for example from cultures of thymocytes (thymus cells), of fetal calf kidney cells, of leukocytes, of hybrid cells, of fibroblasts etc. Of course, not only the cell cultures as such, but also washed cell masses from the appropriate cultures can be employed as the starting material.

The process imposes no restriction on the origin and pretreatment of the starting material. The biological action of the extract is not restricted to a particular class of substance or a particular indication. The extract produced by this process can be separated into fractions by further steps, and pure substances can be isolated therefrom.

(a) Comminution and disintegration of the cells

The organs or cell cultures are in every case procured with due attention to strict instructions for low-germ or sterile working. In the case of animal organs, the defatted material is worked up, namely comminuted and disintegrated, immediately after having been obtained. If this is not immediately possible, the material is cooled to a low temperature, for example to −25° C. or even in liquid nitrogen, and is stored in this state until it is worked up; this inactivates the bacteria and enzymes contained therein. The organs, whether deep-frozen or not, are then chopped in a mincer to form a fine slurry and the cells are disintegrated by dilution in a 1:1 (weight/volume) ratio with pyrogen-free, sterile and doubly distilled water.

In the case of cell cultures, the procurement and, where relevant, storage of the material are to be carried out under sterile conditions. The comminution and disintegration are preferably effected by ultrasonics. The sonication should be carried out with cooling, preferably at a temperature of about 0° to about 10° C.

(b) Protein precipitation by heating

The slurry is heated in a flow-through system and subsequently cooled in a second, similar system. In these systems, the slurry flows through a spiral steel tube located in a jacket through which heat-transfer medium or cooling medium flows. The flow rate of the slurry can be controlled. Compared to conventional heating in a round-bottomed flask, this process permits substantial timesaving and achieves reproducible protein precipitation.

This type and method of heat denaturation indeed offers various specific advantages. The effective and rapid heat exchange between the heating or cooling medium and the product, which for its part is constantly being mixed in the tube by a mixing system so that all particles are warmed uniformly, permits continuous operation with quantities of any desired magnitude.

The modular construction system of the heat exchanger permits several conditions of operation to be adapted to the sensitivity of the product and the particular requirements. Thus:

the temperature can be regulated,
the residence time or reaction times can be regulated and
the temperature increase can also be effected stepwise.

This method of construction thus permits gentle and both physically and biochemically optimal treatment of the product.

The rapid temperature exchange reduces the working time, for example the time required for heat denaturation, by 75% or more compared to the conventional methods employing a round-bottomed flask. As a result, not only time but also energy is saved, as the result of the greater efficiency.

(c) Removal of the precipitated material

The solid and liquid phases are separated by centrifuging, advantageously in a decanter. Since only relatively small amounts can be separated with a laboratory centrifuge (a full 2 hours are required for 10 liters), the use of a flow-through system has proved particularly advantageous not only for this process step but also for continuous production. For example, a high-speed decanter from Flottweg Werk (Dr. Georg Bruckmayer GmbH & Co. KG, Vilsbiburg, Federal Republic of Germany) is used. While the solids may be useful for byproducts, the liquid phase is passed to the next step.

(d) Ultrafiltration using a hollow fiber system

To the clarified aqueous solution from the decanter are added successively, for example, 3 volumes of pyrogen-free, sterile and doubly distilled water, and the material is subjected to ultrafiltration. The ultrafiltration can also be carried out with continuous addition of several volumes of water. This has the advantage that the filtration gives an optimal yield of constituents of molecular weight < 10,000 under substantially constant conditions. Regulating the flow rate and the pressure also has an effect on the quality and quantity of the substances contained in the filtrate. The ultrafiltration is carried out in a hollow fiber ultrafiltration unit of the Romicon HF type [manufactured by Romicon Inc., Woburn (MA, USA)] or of the Amicon type [manufactured by Amicon Corporation, Danvers (MA, USA], with 4 cartridges each of 2.5 m$^2$ membrane surface. All molecules of molecular weight > 10,000 Daltons are separated off. Per hour, 160 liters can be ultrafiltered at 4° C. The continuous dilution has the effect that virtually all small molecules filter through.

A further advantage of the process is that the three steps discussed above, namely b, c and d, can be combined in one system, thereby permitting continuous production. Each installation can be used individually or connected up again in series to the heat exchanger.

The ultrafiltrate obtained is then brought to a small volume, for example by vacuum distillation. Preferably, it is concentrated to between one-tenth and one-twentieth of the original volume.

(e) Electrodialysis

The dissolved salt ions are removed from the concentrated ultrafiltrate in an electrodialysis apparatus (for example Model BEL II from Berghof GmbH, Tübingen, Federal Republic of Germany) by applying a potential difference in an electric field. The smallest singly-charged ions migrate most rapidly, thus offering the advantage of a method with some selectivity. Moreover, only ions of molecular weight <400 migrate through the membrane. The desalting effect depends on the time, on the potential difference applied, on the quality of the membranes and on the composition of the extract. Various factors in the extract influence the theoretical bases of the electrodialysis process, so that the optimal conditions for desalting an extract cannot be calculated, given the large number of unknowns, and must be established from experience. It is definite however that the small salt ions such as $Cl^-$ and $Na^+$ can be removed virtually quantitatively from the extract in the space of 2 hours. However, the optimum need not necessarily correspond to 100% desalting in respect of $Cl^-$ and $Na^+$ ions, since the accompanying loss of other slowly migrating small ions such as aminoacids, peptides and the like may mean a loss in biological activity.

Because the potential cannot be increased indefinitely (due to electrolysis occurring), the membranes must be cleaned by pole reversal and washing after an amount or organ extract, which varies with the particular apparatus, has been dialyzed. It has also been found that the electrodialysis takes place more rapidly at a temperature in the range from 30° to 40° C., and at about 37° C. even takes place three times as rapidly as at 20° C., without thereby causing differences in the product. In addition to increasing the ion transport activity, this temperature increase reduces the effectiveness of polarization and reduces the deposition of uncharged or organic charged molecules (referred to as fouling), which phenomena modify the ion-selective membrane.

Since the energy employed in removing the ions is to a large extent converted to heat, only an insignificant amount of additional energy is needed to maintain a temperature of 37° C. and this, together with the reduction in time required, has an advantageous effect on the production process.

It is known that the column chromatography desalting which hitherto has generally been employed is very expensive and suffers from a very great danger of bacterial contamination, especially at neutral pH values; moreover, in column chromatography desalting various biologically active substances are separated off with the salt fraction. This immediately shows the advantages associated with desalting by electrodialysis.

The complete extracts obtained according to the invention are tested for sterility, pyrogenicity and antigenicity by the following methods:
Sterility: U.S. Pharmacopoeia XX (1980), pages 878–882 European Pharmacopoeia, 2nd Edition, 1st Supplement, 1980, pages 52–55
Pyrogenicity: European Pharmacopoeia, Volume II, Swiss Edition, pages 56–59
Antigenicity: U.S. Pharmacopoeia XX (1980), page 688 (modified for a dialysate)

The biological effects of the extracts can be demonstrated in the Warburg test, by increase of respiration of liver homogenisates or by normalization of the proliferation of cultures of reversibly damaged fibroblasts. In clinical testing, the complete spleen extract and the complete thymus extract display a regulating or normalizing action on a human disturbed immune system.

The biological effects mentioned are shown in Tables 1 and 2 and in FIGS. 2, 3 and 4 for the extracts prepared according to the examples given below.

BRIEF DESCRIPTION OF THE DRAWINGS

FIG. 6 shows a spleen extract, FIG. 7 a thymus extract.

TABLE 1

Factor of increase in $O_2$ consumption produced by the complete extract (10 mg of test substance/ml) in the Warburg test

| Time of measurement | Blank without test substance | Comparative preparation | Spleen (calf) | Thymus (calf) | Bone marrow (calf) | Spinal marrow (calf) | Blood serum (calf) | Blood (calf) | Defibrinated blood (calf) | Placenta (sheep) |
|---|---|---|---|---|---|---|---|---|---|---|
| 30 min. | 1 | 2.2 | 2.7 | 3.9 | 2.5 | 2.6 | 2.2 | 1.9 | 2.0 | 2.7 |
| 45 min. | 1 | 2.3 | 2.7 | 4.0 | 2.5 | 2.7 | 2.3 | 1.9 | 2.1 | 2.8 |
| 60 min. | 1 | 2.5 | 2.8 | 4.1 | 2.6 | 2.9 | 2.3 | 2 | 2.2 | 3.0 |

Method:
1.1 ml of Sorensen buffer; 1.0 ml of liver homogenisate; 0.2 ml of test solution; 0.2 ml of 10% strength KOH.
Apparatus: Differential respirometer; water bath: 37° C.; shaking frequency 100/min.
Liver homogenisate: 2 g of liver per 15 ml of buffer
Test solutions: 10 mg of test substance per ml
Comparative preparation according to German Patent 1,076,888

TABLE 2

Factor of increase in $O_2$ consumption by complete thymus extract or complete spleen extract in the Warburg test

| Time of measurement | Blank without test substance | Comparative preparation mg/ml | | | Thymus extract mg/ml | | | Spleen extract mg/ml | | |
|---|---|---|---|---|---|---|---|---|---|---|
| | | 50 | 12.5 | 6.25 | 50 | 12.5 | 6.25 | 50 | 12.5 | 6.25 |
| 30 min. | 1 | 4.3 | 2.2 | 1.3 | 5.4 | 4.0 | 2.1 | 5.2 | 3.3 | 1.8 |
| 45 min. | 1 | 4.6 | 2.2 | 1.2 | 5.8 | 4.0 | 1.9 | 5.6 | 3.3 | 1.6 |

TABLE 2-continued

Factor of increase in $O_2$ consumption by complete thymus extract or complete spleen extract in the Warburg test

| Time of measurement | Blank without test substance | Comparative preparation mg/ml | | | Thymus extract mg/ml | | | Spleen extract mg/ml | | |
|---|---|---|---|---|---|---|---|---|---|---|
| | | 50 | 12.5 | 6.25 | 50 | 12.5 | 6.25 | 50 | 12.5 | 6.25 |
| 60 min. | 1 | 4.9 | 2.2 | 1.1 | 6.5 | 4.1 | 1.8 | 6.3 | 3.3 | 1.5 |

Method:
1.1 ml of Sorensen buffer; 1.0 ml of liver homogenisate; 0.2 ml of test solution; 0.2 ml of 10% strenght KOH.
Apparatus: Differential respirometer; water bath: 37° C.; shaking frequency 100/min.
Liver homogenisate: 2 g of liver per 15 ml of buffer
Test solutions: 10 mg of test substance per ml
Comparative preparation according to German Patent 1,076,888

Figure 1:
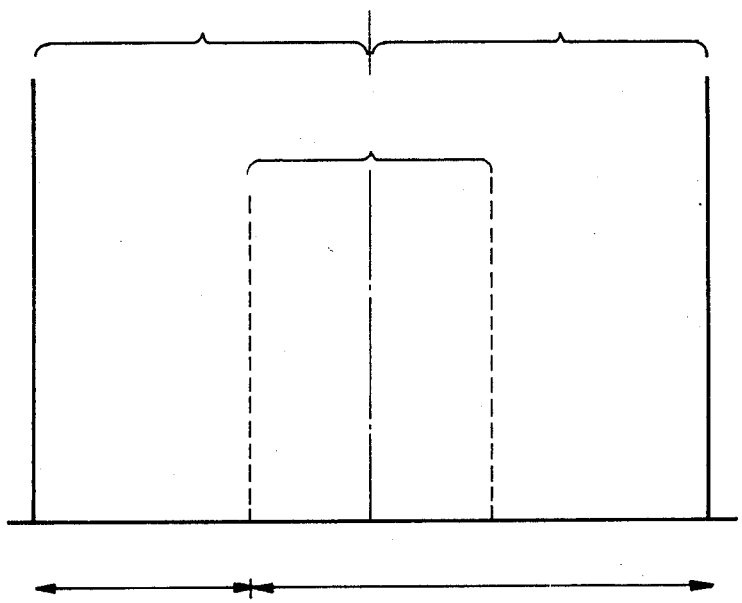
FIG. 1 Demonstrates that salt Ions overlap with both hydrophilic and hydrophobic substances in the starting material.
Figure 2:
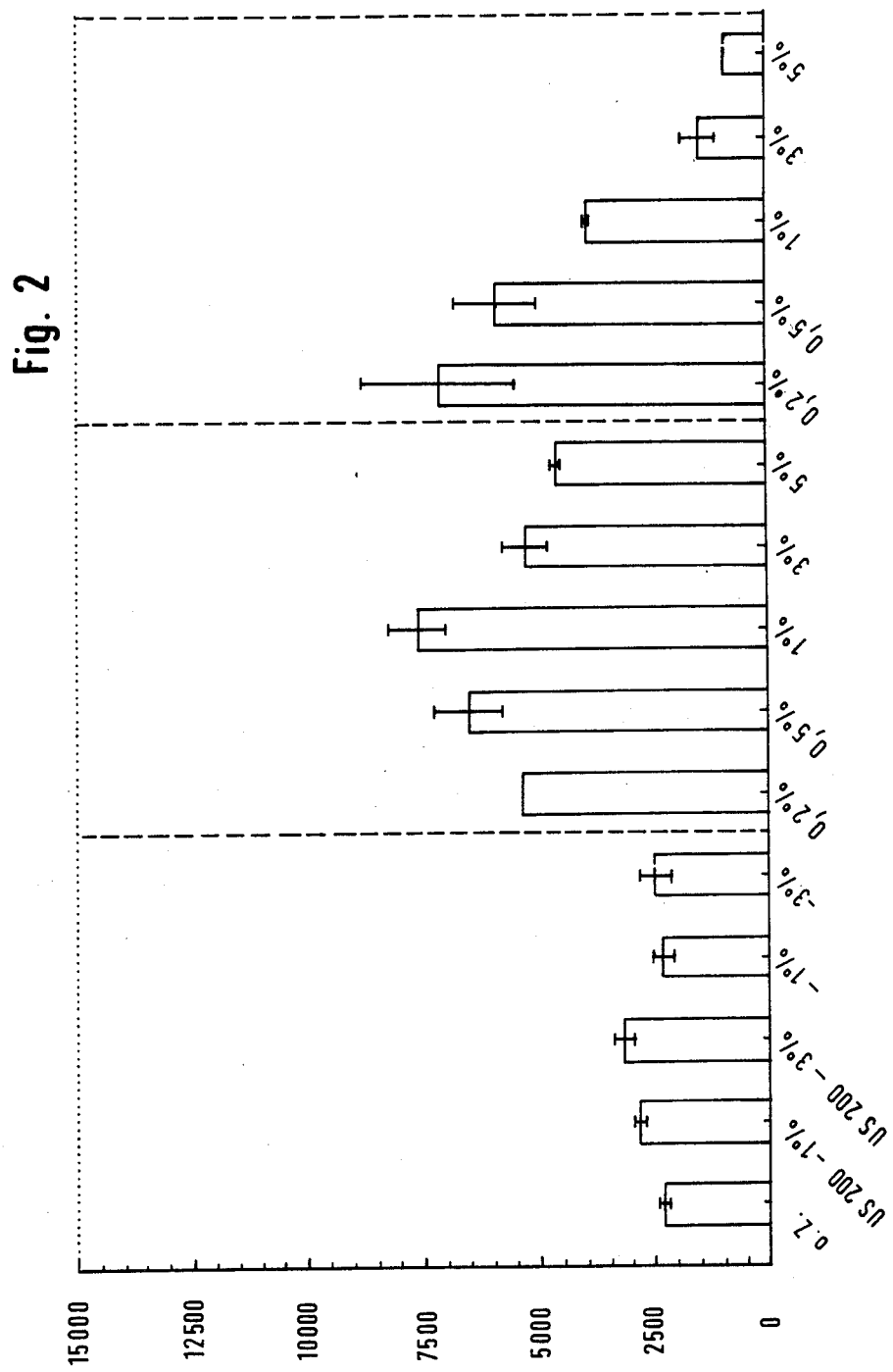
FIGS. 2, 3, 4 Illustrate the incorporation of $H^3$-thymidine into the DNA of damaged fibroblasts after addition of various test solutions.
Figure 3:
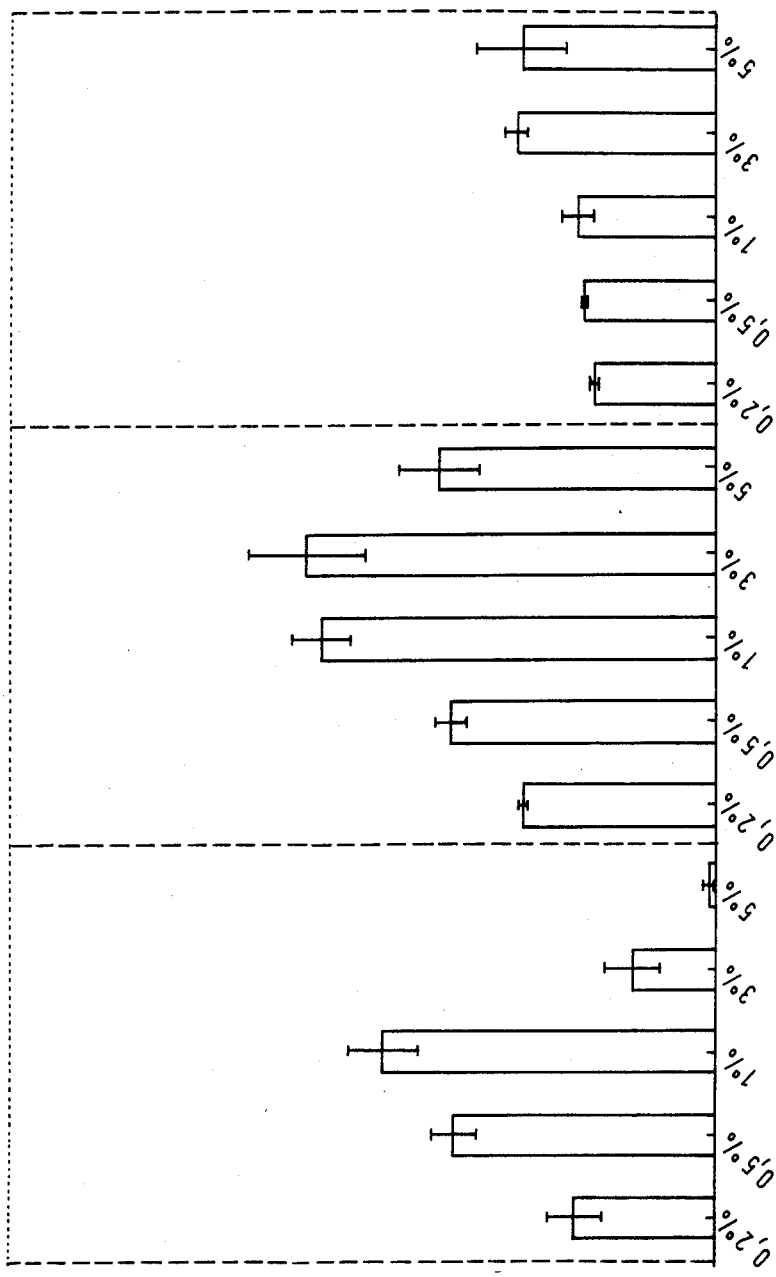
Figure 4:
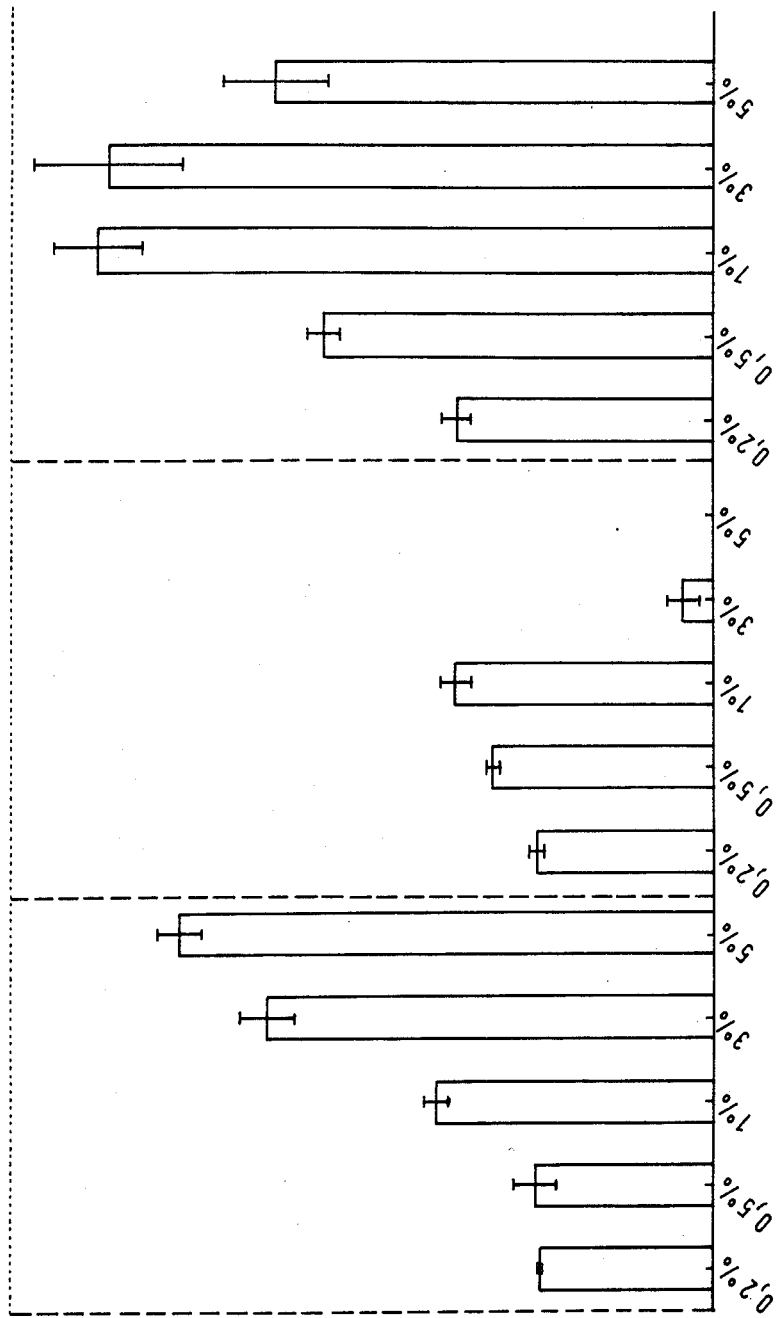

FIGS. 2, 3 and 4 illustrate the incorporation of $^3$H-thymidine into the DNA of damaged fibroblasts after addition of various test solutions. In the growth phase, the fibroblasts are reversibly damaged by carbonate withdrawal. Addition of the test substances normalizes the proliferation of the fibroblasts, as measured by the $^3$H-thymidine incorporation.

The solution of the comparative preparation had a concentration of 42 mg/ml, while all other test solutions contained 10 mg of solids/ml. The comparative preparation was tested at a concentration of 1% and 3% by volume/volume, and all the other products were each tested at 0.2, 0.5, 1, 3 and 5% by volume/volume.

In FIGS. 2, 3 and 4 the abbreviation n.a. means "no additive", US 200 is a comparative preparation according to German Pat. No. 1,076,888 (K.-H. Jaeger) and the placebo consists of a mixture of substances of molecular weight < 10,000 Daltons which usually occur in mammal blood.

Characterization of the process products

High performance liquid chromatography, also referred to as HPLC, is very suitable for the characterization of organ extracts, especially because the method ensures good separation of the individual substances and good reproducibility. As a result, differences in the composition of different products can be established relatively easily. The method also permits adaptation of the system to the particular problem. The standard conditions used are as follows:

Buffer system: 0.01M $(NH_4)H_2PO_4$
Mobile phase A: 0.01M $(NH_4)H_2PO_4$ in 0.1% strength propionic acid
Mobile phase B: 90% strength methanol
Gradient: 0% B to 95% B
Time: 30 minutes
Flow rate: 1.5 ml/min. Pen recorder: 10 mm/min.
Wavelength $\lambda$: 254 nm
Column: RP-8 (manufacturer: E. Merck AG, Darmstadt, Federal Republic of Germany)

Figure 5:
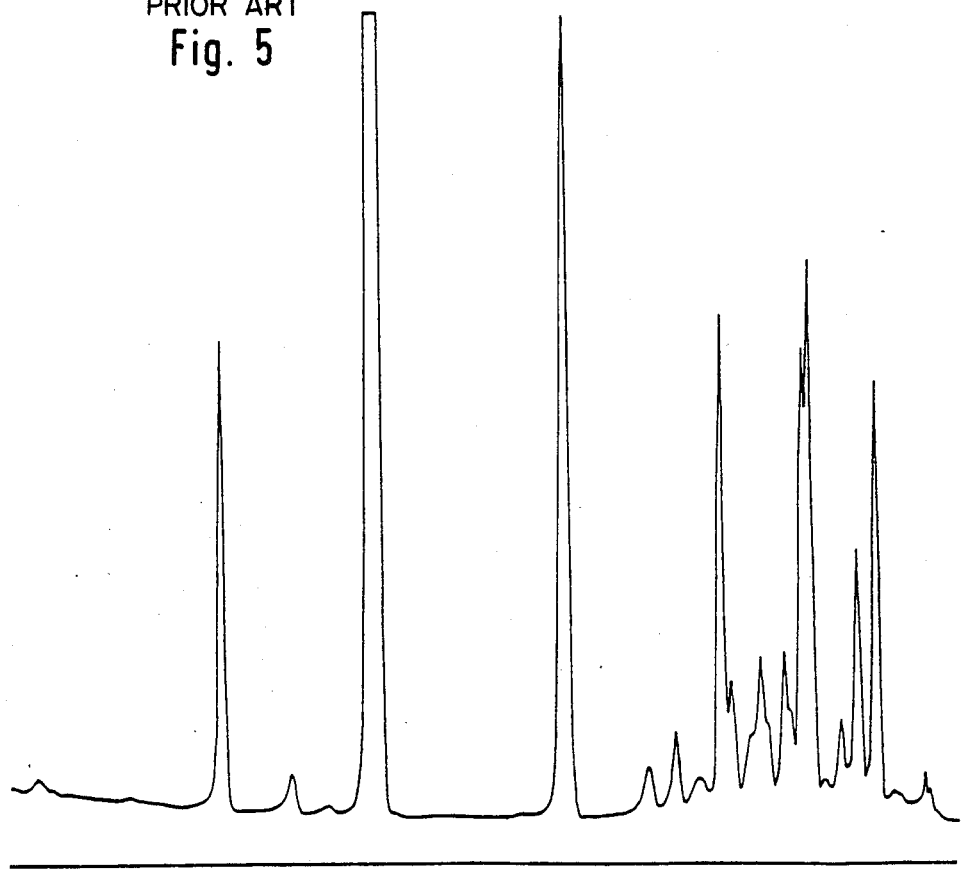
FIG. 5 shows an elution profile of extracts obtained by the prior art process according to German Pat. No. 1,076,888.

This method makes it possible to demonstrate clear differences between the extracts obtained, for example between a spleen extract obtained by the conventional or old dialysis process according to German Pat. No. 1,076,888 (FIG. 5) and one obtained by the novel process according to the invention (FIG. 6):

The diagrams differ especially at two points: at the beginning of the diagram, starting from the right, the old process shows only small peaks compared to the new. The three dominant peaks in the left-hand half of the diagram indicate the preservative (Nipagin/-Nipasol), and these peaks are entirely absent in the new process.

Figure 6:
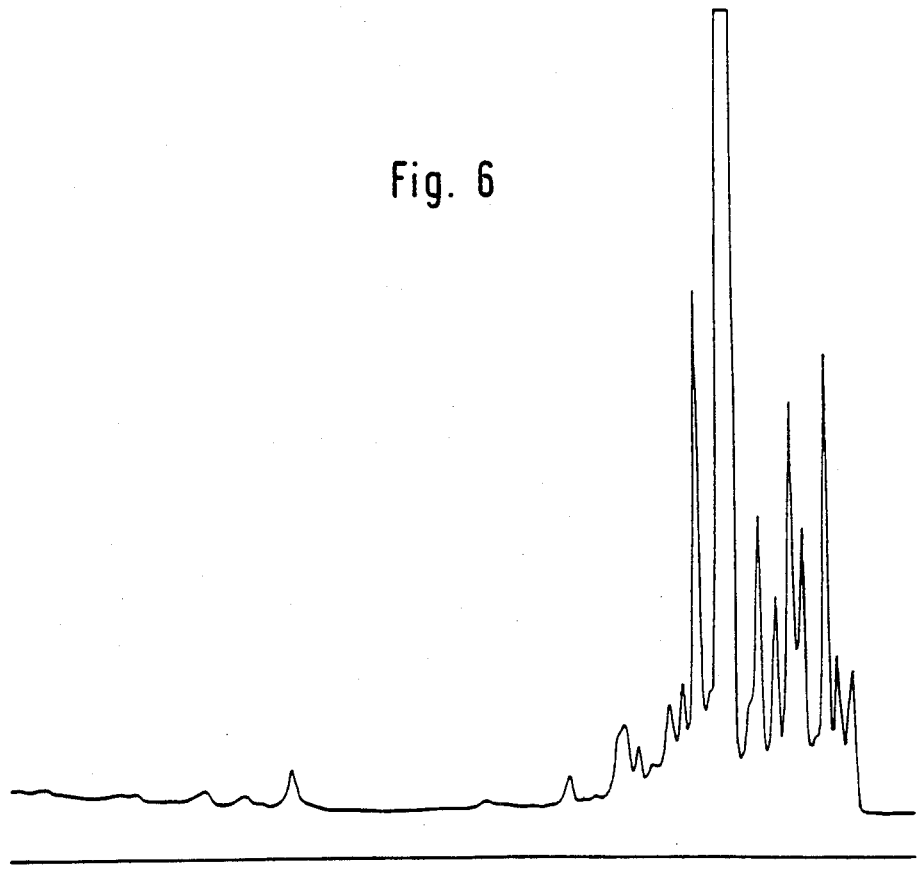
FIGS. 6 and 7, show the elution profiles of extracts obtained by the process of the instant invention.
Figure 7:
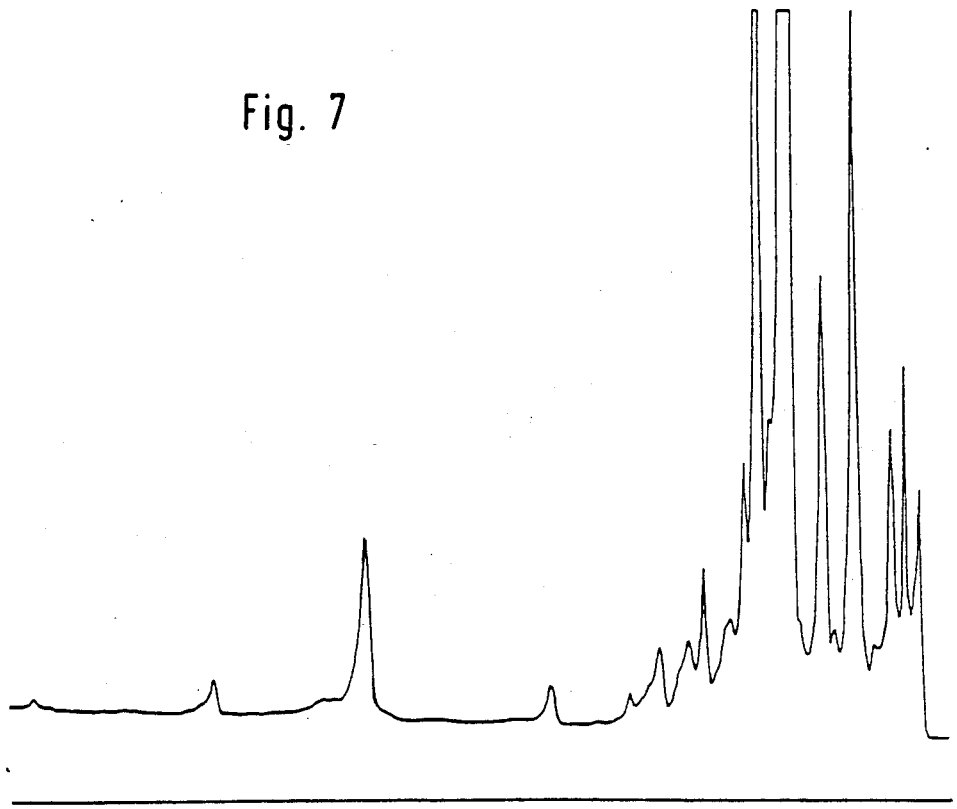
Figure 8:
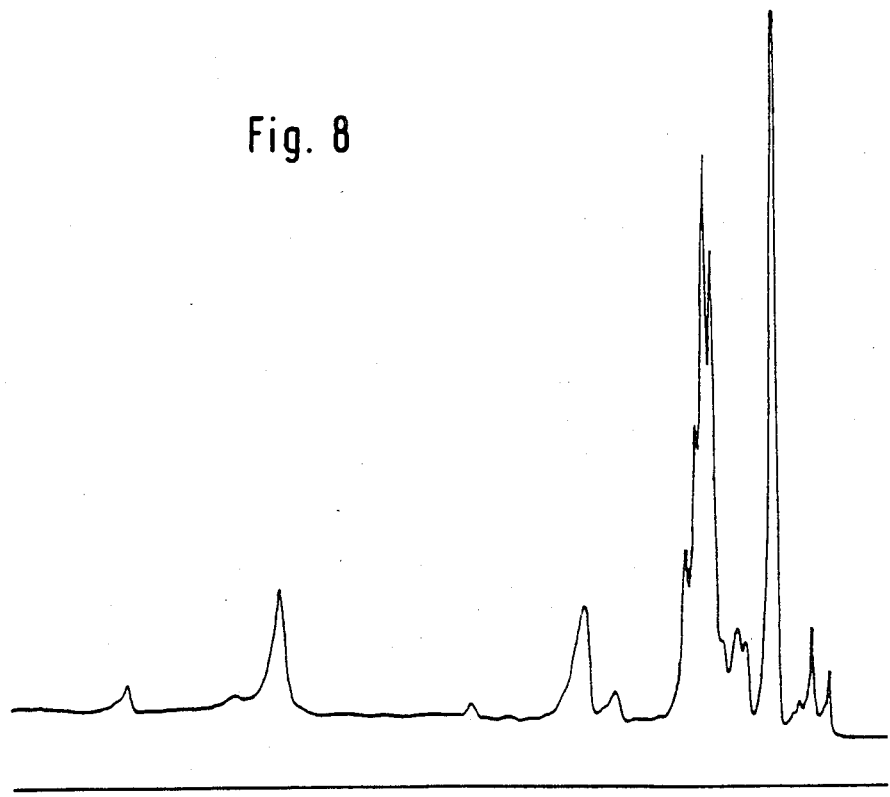
FIG. 8 shows a hydrolized thymus extract elution profile.

The thymus extract prepared according to the invention shows a similar elution profile (FIG. 7) to that of the correspondingly prepared spleen extract (FIG. 6). After hydrolysis of the thymus extract (6N HCl, 18 h, 110° C.) marked peaks disappear (FIG. 8). By fractionation and thin layer chromatography with appropriate staining it is possible to demonstrate that the peaks which have disappeared are attributable to ninhydrin-positive substances.

Further proof that the peptide content is much greater in the extracts obtained by the novel process is provided by isoelectrofocussing (separation in accordance with the isoelectric point). In extracts prepared by the novel process it is possible to detect more than 30 Comassie Blue-positive bands while in the old process only a few weakly colored bands become visible.

EXAMPLE 1: THYMUS 5 kg of calf thymus, deep-frozen immediately, without fatty tissue, and stored at −25° C., are chopped in a mincer to form a slurry. 5 liters of pyrogen-free doubly distilled water are added to the slurry and high molecular weight constituents are precipitated in a flow-through heater for 10 minutes at 80° C. Thereafter, the solid phase is separated out from the cooled slurry by centrifuging (in a centrifuge or decanter). For continuous ultrafiltration, a further 10 liters of pyrogen-free water are added to the supernatant liquor (membrane surface 2.5 m$^2$, PM-10 System Romicon HF ⅓ S). Salt ions are abstracted from the concentrated ultrafiltrate by electrodialysis. A pyrogen-free and antigen-free thymus extract of low salt content is obtained.

EXAMPLE 2: SPLEEN (a) 5 kg of fresh spleen organs of healthy calves are immediately deep-frozen, without fatty tissue. The deep-frozen blocks are converted to a homogeneous slurry in a mincer. The slurry, together with 6 liters of pyrogen-free water, is heated to 80° C. in the course of 3 minutes in a flow-through heater (tube length 5 m) and is kept at a constant temperature of 80° C. by circulating it for 8 minutes. It is then cooled to 4° C. in the course of 6 minutes by means of the flow-through cooler, and the precipitated substances are removed by centrifuging. The supernatant liquor together with 18 liters of pyrogen-free water is continuously ultrafiltered (molecular weight < 10,000 Daltons). The salt ions are substantially removed from the concentrate by electrodialysis. The tests, carried out after all stages of the process, to determine microorganism growth proved negative.

(b) 250 kg of fresh spleen organs of healthy calves are immediately deep-frozen, without fatty tissue. The deep-frozen blocks are converted to a homogeneous slurry in a mincer and the slurry together with 250 liters of pyrogen-free water is then heated to 80° C. in a flow-through heater (tube length 20 m) in the course of 5 minutes (5 min. = dwell time of a particle in the tube), after which the mixture is cooled at 4° C. in the course of 6 minutes in the flow-through cooler. The solid precipitated substances are separated off in the downstream decanter. The aqueous supernatant liquor, with addition of 900 liters of pyrogen-free water, is continuously ultrafiltered (molecular weight < 10,000 Daltons). The ultrafiltrate is concentrated in a circulatory evaporator and is subsequently sterile-filtered. Salt ions are removed from the concentrate, treated in portions, in an electrodialysis process, so that a low-salt aqueous solution of low molecular weight substances from the spleen is produced. The process is carried out in a closed system.

EXAMPLE 3: CALF'S BLOOD SERUM 3 liters of pyrogen-free water are added to 6 liters of serum from fresh calf's blood. This suspension is heated to 75° C. in a flow-through heater, kept for 5 minutes at the same temperature and then cooled to 4° C. by means of the same tube system. The precipitated substances are removed by centrifuging. The supernatant liquor, amounting to 5.5 liters, is continuously ultrafiltered (molecular weight < 10,000 Daltons) with 15 liters of pyrogen-free water. After the salts have been substantially removed by electrodialysis, a sterile and pyrogen-free solution is obtained. This low molecular weight serum extract produces normalization of proliferation of fibroblasts reversibly damaged in a culture.

EXAMPLE 4: FRESH CALF'S BLOOD 5 liters of fresh calf's blood are mixed with 5 liters of pyrogen-free water and the mixture is heated to 80° C. in a flow-through heater. After is has been kept for 3 minutes at the same temperature, the suspension is cooled to 4° C. in a flow-through cooler and the precipitated products are removed by centrifuging. The supernatant liquor, amounting to 6 liters, is continuously ultrafiltered (molecular weight < 10,000 Daltons) with 18 liters of pyrogen-free water. After substantial elimination of the salts by electrodialysis, a sterile and pyrogen-free solution is obtained. The low molecular weight calf blood extract thus obtained produces normalization of proliferation of fibroblasts damaged in a culture.

EXAMPLE 5: DEFIBRINATED CALF'S BLOOD 5.1 kg of defibrinated calf's blood and 5 liters of pyrogen-free water are heated to 80° C. in a flow-through heater and kept at the same temperature for 5 minutes. The slurry is then cooled to 4° C. in a flow-through cooler and the precipitate is removed by centrifuging. The supernatant liquor, amounting to 7 liters, is continuously ultrafiltered (molecular weight < 10,000 Daltons) with 18 liters of pyrogen-free water. After electrodialysis, a low-salt, sterile and pyrogen-free concentrated solution is obtained. This solution produces normalization of proliferation of fibroblasts reversibly damaged in a culture.

EXAMPLE 6: CALF'S SPINAL MARROW 5 kg of marrow are isolated from the vertebrae of freshly slaughtered healthy calves. The marrow is heated with 5 liters of pyrogen-free water to 80° C. in a flow-through heater and kept at the same temperature for 5 minutes. The slurry is then cooled to 4° C. in a flow-through cooler. It is then centrifuged, after which ⅓ of the volume can be employed directly, as supernatant liquor, for the next stage. These 3 liters are ultrafiltered (molecular weight < 10,000 Daltons) with 9 liters of pyrogen-free water. The concentrate is reduced in volume and salt ions are removed from it by electrodialysis. The low-salt solution was sterile and pyrogen-free. In fibroblasts reversibly damaged in a culture, the solution produced normalization of proliferation, while in bone marrow cells it produced an increase in the activity of the terminal deoxytransferase.

EXAMPLE 7: MARROW FROM FEMUR BONES

A slurry of 3.5 kg of marrow from 30 kg of femur bones of freshly slaughtered calves is heated with 5 liters of pyrogen-free water to 75° C. in a flow-through heater. The suspension is kept at 75° C. for 5 minutes. When it has been cooled to 4° C. in a flow-through cooler, the solidified fat is separated from the rest of the solution. The defatted solution is centrifuged and the supernatant liquor, amounting to 5 liters, is continuously ultrafiltered (molecular weight < 10,000 Daltons) with 15 liters of pyrogen-free water. Salt ions are removed from the concentrated product by electrodialysis. The low-salt solution is sterile and pyrogen-free. In fibroblasts reversibly damaged in a culture it produces a normalization of proliferation, and also produces an increase in activity of terminal deoxytransferase.

EXAMPLE 8: SHEEP'S PLACENTA 4.700 kg of a slurry from deep-frozen rosettes of fresh sheep's placenta and 5 liters of pyrogen-free water are heated to 80° C. in a flow-through heater and kept at this temperature for 5 minutes, while being circulated. The slurry is then cooled to 4° C., the precipitate is removed by centrifuging and the supernatant liquor, amounting to 7 liters, is continuously ultrafiltered (molecular weight < 10,000 Daltons) with 10 liters of pyrogen-free water. The low-salt solution obtained by electrodialysis was sterile and pyrogen-free. It produces normalization of proliferation of fibroblasts reversibly damaged in a culture.

EXAMPLE 9: THYMOCYTES 10 kg of fresh thymus organs of calves together with 10 liters of phosphate-buffered sodium chloride solution (pH 7.2) are triturated in a fine-mesh sieve, using a rubber bung. This detaches the thymocytes from the organ tissue; the residual tissue constituents are discarded. The thymocytes are subsequently washed twice with phosphate-buffered sodium chloride solution and thereafter taken up in 10 liters of doubly distilled, pyrogen-free water ($18 \times 10^8$ cells/ml). 100 ml portions of the thymocytes are disintegrated and comminuted by ultrasonics (Soniprep 150: amplitude 4, medium frequency) for 1 minute. The thymocyte slurry is heated to 80° C. with a further 10 liters of doubly distilled, pyrogen-free water in a flow-through heater and after 10 minutes the mixture is again cooled to 10° C. The denatured proteins and other insoluble cell fragments are separated off by centrifuging in a Sorvall centrifuge with TZ-28 flow-through rotor (20,000 rpm, residence time 10 minutes). The supernatant liquor is then continuously ultrafiltered (exclusion limit molecular weight > 10,000) with a further 20 liters of doubly distilled, pyrogen-free water. The ultrafiltrate is concentrated to 2,000 ml and electrodialyzed. The peptide-containing product shows a growth-promoting activity in $CO_2$-damaged fibroblasts.

EXAMPLE 10: FETAL CALF'S KIDNEY CELLS

Epithelial cells of fetal calf's kidneys (FCK) are cultured in 850 ml roller flasks with "minimal essential medium" [Science 130, 432 (1959)] and 7% fetal calf's serum. Shortly before a continuous cell lawn forms, the cell lawns are washed with phosphate-buffered sodium chloride solution (pH 7.2), released from the roller flasks by means of ethylenediamine tetraacetate and water, using a rubber scraper, and taken up in a total of 4 liters of doubly distilled, pyrogen-free water. The FCK cells ($4 \times 10^8$/ml), in 100 ml portions, are disintegrated and comminuted by means of ultrasonics (Soniprep 150: amplitude 4, medium frequency) for 1 minute. The FCK cell slurry, together with a further 4 liters of water, is heated to 80° C. in a flow-through heater and after 10 minutes the mixture is again cooled to 10° C. The denatured protein and other insoluble cell fragments are removed in a Sorvall centrifuge with TZ-28 flow-through rotor (20,000 rpm, residence time 10 min.). The supernatant liquor is then continuously ultrafiltered (exclusion limit molecular weight > 10,000) with a further 8 liters of doubly distilled, pyrogen-free water. The ultrafiltrate is concentrated to 500 ml and electrodialyzed. The peptide-containing product shows a growth-promoting activity in $CO_2$-damaged fibroblasts.

We claim:

1. A process for the preparation of a biologically active, low-salt, pyrogen-free, sterile and antigen-free complete extract of mammal organs and of cell cultures, the extract consisting of a mixture of biologically active substances having a molecular weight of less than 10,000 Daltons, which comprises comminuting with disintegration of the cells the starting material which has been procured, and may have been stored, under low-germ or sterile conditions, rapidly heating the comminuted and disintegrated material in a heat exchanger to a temperature from 70° to 90° C. and rapidly again cooling to a low temperature, separating the products thereby precipitated from the solution by centrifugation, removing the substances having a molecular weight of greater than 10,000 Daltons from the solution by ultrafiltration and removing the salt ions from the remaining solution by electrodialysis, the whole process being carried out with exclusion of any foreign substances other than water, and without the use of any carrier material for separation methods.

2. A process as claimed in claim 1, wherein the starting material used is mammal thymus, spleen, liver, heart, placenta, bone marrow or blood.

3. A process as claimed in claim 2, wherein the starting material is the thymus.

4. A process as claimed in claim 1, wherein the starting material is a culture of thymocytes, of fetal calf's kidney cells, of leukocytes, of hybrid cells or of fibroblasts or is a cell mass obtained from the corresponding culture.

5. A process as claimed in claim 1, wherein the comminution and the disintegration of the cell culture is effected by the action of ultrasonics.

6. A process as claimed in claim 1, wherein the electrodialysis is carried out at a temperature in the range from 30° to 40° C.

7. A process as claimed in claim 1, wherein the steps of heat treatment, removal of the precipitated products and ultrafiltration are carried out in a continuous process.

8. A process as claimed in claim 1, wherein the complete extract obtained is additionally subjected to a sterilization.

* * * * *